United States Patent [19]

Matsuishi et al.

[11] Patent Number: 4,753,955
[45] Date of Patent: Jun. 28, 1988

[54] BENZIMIDAZOLE DERIVATIVES

[75] Inventors: Naoto Matsuishi, Kawaguchi; Haruki Takeda, Kamisato; Kenichi Iizumi, Mitaka; Kiyokazu Murakami, Yokohama; Akira Hisamitsu, Omiya, all of Japan

[73] Assignee: Tokyo Tanabe Company, Ltd., Japan

[21] Appl. No.: 12,897

[22] Filed: Feb. 10, 1987

[30] Foreign Application Priority Data

Feb. 28, 1986 [JP] Japan .................................. 61-41879

[51] Int. Cl.$^4$ ..................... C07D 401/12; A61K 31/44
[52] U.S. Cl. ..................................... 514/338; 546/271
[58] Field of Search ......................... 546/271; 514/338

[56] References Cited

U.S. PATENT DOCUMENTS 4,472,409 9/1984 Senn-Bilfinger ................ 546/271

Primary Examiner—Jane T. Fan

Attorney, Agent, or Firm—McGlew and Tuttle

[57] ABSTRACT

Benzimidazole derivatives of the general formula [I] are provided:

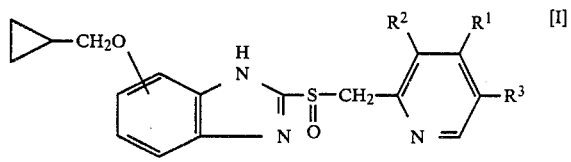

wherein $R^1$ is hydrogen, methyl or methoxy, and $R^2$ and $R^3$ each is hydrogen or methyl, at least one of $R^1$, $R^2$ and $R^3$ being a member other than hydrogen. The benzimidazole derivatives exhibit an excellent activity of inhibiting the potassium ion-dependent adenosine triphosphatase, as well as a good stability during storage. Therefore, the benzimidazole derivatives are usable for the treatment of gastric and/or duodenal ulcers.

34 Claims, No Drawings

BENZIMIDAZOLE DERIVATIVES

BACKGROUND OF THE INVENTION

(1) Field of the Invention

The present invention relates to benzimidazole derivatives having a cyclopropylmethyloxy group on the benzene ring, processes for preparing such compounds, and pharmaceutical compositions such a compound as an active ingredient. The benzimidazole derivatives according to the present invention exhibit excellent stability during storage and can be used for the treatment of gastric and duodenal ulcers.

(2) Description of the Prior Art

In recent years, the behavior of the potassium ion-dependent adenosine triphosphatase [hereinafter referred to as "(H+ +K+)-ATPase"], which takes part in the production of hydrochloric acid in the vesicles of gastric endoplasmic reticulum, has received attention in the pathologic physiology of gastric and duodenal ulcers, and the activity of inhibiting the enzyme has become an indicator for antiulcer agents [Gastroenterology, Vol. 1, p. 420 (1943); and ibid., Vol. 73, p 921 (1977)]. From the above viewpoint, extensive clinical investigation has been made on 5-methoxy-2-[2-(4-methoxy-3,5-dimethyl)-pyridylmethylsulfinyl]benzimidazole (hereinafter referred to as "omeprazole") [Japanese Patent Laid-Open No. 141,783/79; and British Medical Journal, Vol. 287, p. 12 (1983)].

However, a problem arises on the stability of omeprazole, since it is degraded at an unexpectedly high rate when stored without any special precautions being taken. In order to solve this problem, it is required to convert omeprazole into its salts (Japanese Patent Laid-Open No. 167,587/84).

SUMMARY OF THE INVENTION

In view of the above, the inventors have conducted intensive investigations on various omeprazole-related compounds. As a result, it has been found that benzimidazole derivatives having a cyclopropylmethyloxy group on the benzene ring possess a sufficient stability during storage even in the cases where they are not converted into their salts. It has also been found that the benzimidazole derivatives, when orally administered, provide a gastric antisecretory effect based on its (H+ +K+)-ATPase inhibition activity which is superior to that of omeprazole. The present invention has been accomplished on the basis of the above findings.

According to one feature of the present invention, there is provided a benzimidazole derivative represented by the following General Formula [I]:

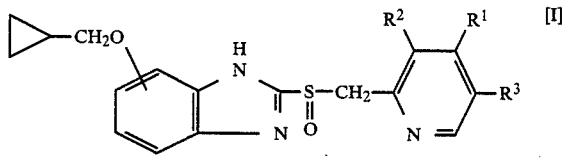

(wherein $R^1$ is a hydrogen atom, a methyl group or a methoxy group, and $R^2$ and $R^3$ each is a hydrogen atom or a methyl group, at least one of said $R^1$, $R^2$ and $R^3$ groups being a member other than a hydrogen atom).

According to another feature of the present invention, there is provided a process for preparing benzimidazole derivatives represented by the above General Formula [I].

According to still another feature of the present invention, there is provided a pharmaceutical composition containing a benzimidazole derivative represented by the above General Formula [I], as an active ingredient.

DETAILED DESCRIPTION OF THE PREFERRED EMBODIMENTS

The benzimidazole derivatives represented by the above-described General Formula [I] (hereinafter referred to briefly as the present compounds [I]) can be prepared by oxidizing a sulfide compound represented by the following General Formula [II]:

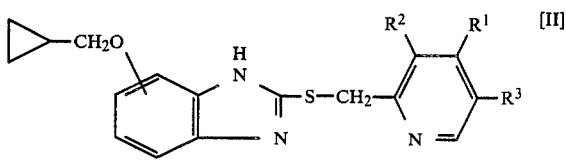

(wherein $R^1$, $R^2$ and $R^3$ have the same meanings as above) by use of an oxidizing agent in the presence of a solvent. As examples of usable solvents, mention may be made of halogenated hydrocarbons, such as chloroform and dichloromethane; alcohols, such as methanol, ethanol, propanol and butanol; and mixtures of two or more of these solvents. The use of chloroform or dichloromethane can be preferable with regard to yield attainable. As examples of usable oxidizing agents, mention may be made of peroxides, such as m-chloroperbenzoic acid, perbenzoic acid and peracetic acid. Of these peroxides, m-chloroperbenzoic acid can be preferable with regard to stability. In said oxidation reaction, there may be used 1.0 to 1.3 moles of oxidizing agents, per mole of said sulfide compounds [II]. The reaction may be carried out at a temperature of from $-70°$ to $30°$ C., preferably from $-20°$ to $10°$ C., for a period of from 1 minute to 24 hours, preferably from 5 minutes to 1 hour.

The sulfide compounds [II] can be prepared by condensing a thiol compound represented by the following General Formula [III]:

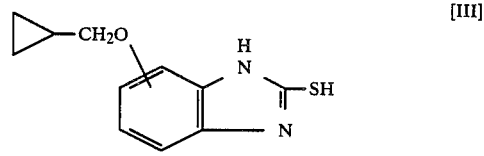

with a pyridine compound represented by the following General Formula [IV]:

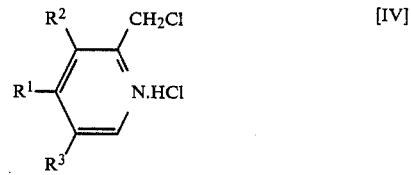

(wherein $R^1$, $R^2$ and $R^3$ have the same meanings as above) in a reaction solvent in the presence of a base. As examples of usable reaction solvents, mention may be made of alcohols, such as methanol, ethanol, propanol and butanol; polar aprotic solvents, such as dimethylformamide and dimethylsulfoxide; water; and mixtures of two or more of these reaction solvents. As examples of usable bases, mention may be made of sodium hydrogen carbonate, sodium carbonate, potassium carbonate, sodium hydroxide and potassium hydroxide. In said condensation reaction, there may be used about 1 mole of said pyridine compounds [IV] and about 2.0 to 3.0 moles of bases, per mole of said thiol compounds [III]. The reaction may be carried out at a temperature of from 10° to 200° C., preferably from 60° to 80° C., for a period of from 1 minute to 12 hours, preferably from 5 minutes to 4 hours.

The starting materials, or thiol compounds [III], can be prepared by reacting 3- or 4-cyclopropylmethyloxy-o-phenylenediamine with potassium xanthogenate in accordance with the method described in Organic Syntheses Collective Vol. 4, p. 569 (1963).

The stability during storage, the $(H^+ +K^+)$-ATPase inhibition activity, the gastric antisecretory effect and the acute toxicity of the present compound [I] will hereinafter be explained in detail. The following tests were carried out by using typical examples of the present compounds [I] (hereinafter referred to as test compounds), whose names are set forth below with their example numbers in parentheses.

2-[2-(3,5-dimethyl)pyridylmethylsulfinyl]-5-cyclopropylmethyloxybenzimidazole (Example 1);

2-[2-(4-methyl)pyridylmethylsulfinyl]-5-cyclopropylmethyloxybenzimidazole (Example 2);

2-[2-(3,5-dimethyl)pyridylmethylsulfinyl]-4-cyclopropylmethyloxybenzimidazole (Example 3);

2-[2-(3,4,5-trimethyl)pyridylmethylsulfinyl]-5-cyclopropylmethyloxybenzimidazole (Example 4);

2-[2-(3,4,5-trimethyl)pyridylmethylsulfinyl]-4-cyclopropylmethyloxybenzimidazole (Example 5);

2-[2-(4-methoxy-3,5-dimethyl) pyridylmethylsulfinyl]-4-cyclopropylmethyloxybenzimidazole (Example 6);

2-[2-(4-methoxy-3,5-dimethyl) pyridylmethylsulfinyl]-5-cyclopropylmethyloxybenzimidazole (Example 7);

2-[2-(4-methoxy-5-methyl)pyridylmethylsulfinyl]-5-cyclopropylmethyloxybenzimidazole (Example 8); and 2-[2-(4-methoxy-5-methyl)pyridylmethylsulfinyl]-4-cyclopropylmethyloxybenzimidazole (Example 9).

(a) Stability During Storage

The stability during storage of the present compounds [I] was tested by allowing each of the test compounds to stand under severe conditions (at a temperature of 60° C. and at a relative humidity of 75%) for 6 days and then determining their residual rates by means of thin layer densitometry in accordance with the method described in Bunseki Kagaku Vol. 23, No. 9, p. 1016 (1974). In the thin layer densitometry, spots each containing 100 μg of a test sample were applied onto thin layer plates. The spots were developed with a mixture of chloroform and ethanol (10:1, by volume). As the thin layer plates, TLC Plate Silica Gel 60 $F_{254}$ (10×20 cm, 0.25 mm in thickness, a product of Merck & Co., Inc.) was used. The distance of development was 15 cm. The densitometry was effected by use of a Shimadzu Dichroic Chromatoscanner CS-910 (manufactured by Shimadzu Corporation) at a wavelength of 280 or 300 nm.

The results obtained are shown in Table 1. In the table is also shown, for the purpose of comparison, the residual rate of omeprazole which was determined in the same manner as above.

TABLE 1

| Compounds | Stability During Storage (60° C., 75% R.H., 6 Days) Residual Rate (%) |
|---|---|
| Omeprazole | 5 |
| Example 1 | 91 |
| Example 2 | 59 |
| Example 3 | 88 |
| Example 4 | 94 |
| Example 5 | 86 |
| Example 6 | 67 |
| Example 7 | 37 |
| Example 8 | 32 |
| Example 9 | 76 |

It would be apparent from Table 1 that the present compounds [I] have far greater stability during storage than that of omeprazole.

(b-1) $(H^+ +K^+)$-ATPase Inhibiting Activity

The $(H^+ +K^+)$-ATPase inhibiting activity of the present compounds [I] was determined in the following manner: A methanol or ethanol solution of a test compound was added to a solution containing 300 to 500 μg (reduced to protein) of said enzyme, so as to make a solution in concentration ranging from $1\times10^{-2}$M to $1\times10^{-4}$M of the test compound; the resulting solution was incubated at a temperature of from 35° to 37° C. for a period of from 5 to 30 minutes to allow the reaction to proceed; and the residual activity of $(H^+ +K^+)$-ATPase contained in the reaction mixture was determined.

The $(H^+ +K^+)$-ATPase used in the above test was prepared from the fundus ventriculi of fresh hog stomachs in accordance with the method of Saccomani et al. [The Journal of Biological Chemistry, Vol. 251, No. 23, p. 7690 (1976)]. The residual activity of $(H^+ +K^+)$-ATPase was determined by incorporating magnesium chloride and potassium chloride into the reaction mixture, adding adenosine triphosphate thereto, incubating the resulting mixture at a temperature of 37° C. for a period of 5 to 15 minutes to allow the enzymatic reaction to proceed, and then colorimetrically determining the liberated inorganic phosphoric acid by the use of ammonium molybdate. The initial concentrations of magnesium chloride, potassium chloride and adenosine triphosphate were 2 mM, 20 mM and 2 mM, respectively. The colorimetric measurement was effected at a wavelength range of from 360 to 400 nm. As a control experiment, the residual activity of $(H^+ +K^+)$-ATPase was determined in the same manner as above without addition of any test compounds. The inhibiting effect was evaluated by the amount of test compound required to inhibit 50% of the $(H^+ +K^+)$-ATPase activity (hereinafter referred to as "$IC_{50}$"). To be more specific, the difference between the colorimetric reading obtained in the control experiment and the colorimetric reading obtained with a test compound is calculated at various molar concentrations, and the difference is divided by the reading of the control experiment to give a rate of inhibition. With inhibition rates thus obtained, a density-inhibition rate curve is plotted, and the $IC_{50}$ value is determined based on the curve. The results obtained are shown in Table 2. In the table is also shown, for the purpose of comparison, the $(H^+ +K^+)$-ATPase inhibiting activity of omeprazole determined in the same manner as above.

TABLE 2

| Compounds | $(H^+ + K^+)$-ATPase Inhibiting Activity IC$_{50}$ (Molar Concentration) |
| --- | --- |
| Omeprazole | $1.8 \times 10^{-3}$ |
| Example 1 | $1.8 \times 10^{-3}$ |
| Example 2 | $2.1 \times 10^{-3}$ |
| Example 3 | $9.0 \times 10^{-4}$ |
| Example 4 | $1.0 \times 10^{-3}$ |
| Example 5 | $1.9 \times 10^{-3}$ |
| Example 6 | $1.9 \times 10^{-3}$ |
| Example 7 | $1.7 \times 10^{-3}$ |
| Example 8 | $3.0 \times 10^{-4}$ |
| Example 9 | $4.3 \times 10^{-4}$ |

(b-2) Gastric Antisecretory Effect

The gastric acid secretion inhibiting effect of the present compounds [I] was tested in the following manner: 1 to 100 mg/kg of a test compound was orally administered at an interval of 5 minutes to a group of 5 male Wistar rats (body weight: ca. 200 g) which had been fasted overnight. Exactly 1 hour after the completion of the administration, the pyloric regions of their stomachs were ligated. After 4 hours, the total acid contained in the gastric juice of each rat was determined.

In the above determination, the test compounds were used in the form of a suspension in a 1:1 (by volume) mixture of polyethylene glycol and aqueous 0.5% carboxymethylcellulose. To collect the gastric juice, the rats were killed, and their stomachs were cut open. The total acid in the gastric juice was determined by titrating the juice with aqueous 0.1N sodium hydroxide solution until its pH reached 7.0. As a control experiment, the total acid contained in the gastric juice of rats not administered with the compounds was also determined in the same manner as above. The gastric antisecretory effect was evaluated by the dosage (mg/kg) required to inhibit the secretion of gastric acid, or total gastric acid, by 50% (hereinafter referred to as ED$_{50}$). In order to determine the ED$_{50}$ value, the difference in total acid between a group of rats administered with a test compound and a group of rats not administered with any of the test compounds was calculated, and the difference was then divided by the total acid of the latter rats, so as to obtain a rate of inhibition. With inhibition rates thus obtained, a dosage-effect curve was plotted, and the ED$_{50}$ value was determined on the basis of the curve. The results obtained are shown in Table 3. In the table is also shown, for the purpose of comparison, the ED$_{50}$ value of omeprazole determined in the same manner as above.

TABLE 3

| Compounds | Gastric Antisecretory Effect ED$_{50}$ (mg/kg) [po] |
| --- | --- |
| Omeprazole | 30.5 |
| Example 1 | 17.8 |
| Example 3 | 19.5 |
| Example 4 | 22.1 |
| Example 8 | 25.9 |

It would be apparent from Tables 2 and 3 that the present compounds [I] have marked $(H^+ + K^+)$-ATPase inhibiting activities and, when orally administered, exert gastric acid secretion inhibiting effects far greater than that of omeprazole.

(c) Acute Toxicity

Using 5 weeks old male Wistar rats, acute toxicity (LD$_{50}$) of two representative compounds (compounds obtained in Examples 1 and 8) of the present compounds [I] was tested. LD$_{50}$ values of the two compounds were not less than 4.0 g/kg when administered orally and not less than 500 mg/kg when administered intraperitoneally.

Taking into consideration the above test results on the stability during storage, $(H^+ + K^+)$-ATPase inhibiting activity, gastric antisecretory effect and acute toxicity, it can be said that the present compounds [I] can be a medicament for treating gastric and/or duodenal ulcers, which medicament is free from deactivation during storage.

The present compounds [I] can be incorporated with physiologically harmless solid or liquid pharmaceutical carriers to prepare pharmaceutical compositions. The compositions can be in the form of solid formulations, such as tablets, capsules, powders, particles and granules, as well as liquid formulations, such as solutions, emulsions and suspensions. In the case where the compositions are solid formulations, they may be provided with coatings, so as to make them soluble in the intestines. Any pharmaceutical carriers normally employed for such formulations may be used therefore, including, for example, excipients, binding agents or disintegrators, such as corn starch, dextrins, $\alpha$-, $\beta$- or $\gamma$-cyclodextrin, glucose, lactose, sucrose, methyl celluloses, ethyl celluloses, carboxymethyl celluloses calcium, crystalline celluloses, magnesium stearate, sodium alginate, Witepsole W35, Witepsole E85, polyvinyl alcohols and synthetic aluminum silicate; lubricating agents or coating agents, such as talc, waxes, hydroxypropyl celluloses, hydroxypropyl methyl celluloses, hydroxyethyl methyl celluloses, cellulose acetate phthalates, hydroxypropyl methyl cellulose phthalates, polyvinyl alcohol phthalates, styrene-maleic anhydride copolymers and polyvinyl acetal diethylaminoacetates; solubilizing atents, such as glycerol, propylene glycol and mannitol; emulsifiers or suspensions, such as polyoxyethylene stearates, polyoxyethylene cetyl alcohol ethers, polyethylene glycols and polyvinyl pyrrolidones; stabilizers, such as sorbitol, Tween 80, Span 60, fats and oils; and various solvents.

In the above pharmaceutical compositions, the present compound [I] can be used at an oral dosage of 0.5 to 2,000 mg, preferably 3 to 200 mg, per day. The thus prepared pharmaceutical compositions according to the invention can be administered 1 to 6 times, preferably 1 to 3 times, a day within the above dosage.

The present invention is further illustrated by the following Reference Example, Examples and Preparation Examples.

REFERENCE EXAMPLE (Preparation of sulfide compounds [II])

To 70 ml of ethanol solution of 0.80 g (0.02 mole) of sodium hydroxide were added 2.20 g (0.01 mole) of 2-mercapto-5-cyclopropylmethyloxybenzimidazole and 1.92 g (0.01 mole) of 2-chloromethyl-3,5-dimethylpyridine hydrochloride, and the resulting mixture was heated under reflux for 3 hours. After the reaction mixture had been cooled to room temerature, the insoluble materials contained therein were filtered off, and the filtrate was condensed under reduced pressure. The residue obtained was dissolved in 100 ml of chloroform and washed with 100 ml of aqueous 5% sodium hydroxide solution. The chloroform layer was dried over anhydrous sodium sulfate and evaporated to dryness under reduced pressure. The residue obtained was purified by means of silica gel column chromatography employing chloroform as the development solvent to give 2.99 g of oily 2-[2-(3,5-dimethyl) pyridylmethylthio]-5-cyclopropylmethyloxybenzimidazole. Yield: 88.1%.

The following 8 compounds were prepared in the same manner as above, except that corresponding thiol compounds [III] (0.01 mole) and pyridine compounds [IV] (0.01 mole) were used in place of 2-mercapto-5-cyclopropylmethyloxybenzimidazole (0.01 mole) and 2-chloromethyl-3,5-dimethylpyridine hydrochloride (0.01 mole).

2-[2-(4-methyl)pyridylmethylthio]-5-cyclopropylmethyloxybenzimidazole: oily substance;

2-[2-(3,5-dimethyl)pyridylmethylthio]-4-cyclopropylmethyloxybenzimidazole: glassy substance;

2-[2-(3,4,5-trimethyl)pyridylmethylthio]-5-cyclopropylmethyloxybenzimidazole: crystals, m.p. 163°–165° C. (recrystallized from a mixture of ethyl acetate and hexane);

2-[2-(3,4,5-trimethyl)pyridylmethylthio]-4-cyclopropylmethyloxybenzimidazole: glassy substance;

2-[2-(4-methoxy-3,5-dimethyl)pyridylmethylthio]-4-cyclopropylmethyloxybenzimidazole: glassy substance;

2-[2-(4-methoxy-3,5-dimethyl)pyridylmethylthio]-5-cyclopropylmethyloxybenzimidazole: crystals, m.p. 133°–134° C. (recrystallized from a mixture of ethyl acetate and hexane);

2-[2-(4-methoxy-5-methyl)pyridylmethylthio]-5-cyclopropylmethyloxybenzimidazole: oily substance; and 2-[2-(4-methoxy-5-methyl)pyridylmethylthio]-4-cyclopropylmethyloxybenzimidazole: crystals, m.p. 142°–143° C. (recrystallized from a mixture of ethyl acetate and hexane).

EXAMPLE 1

In 100 ml of chloroform was dissolved 2.72 g (0.008 mole) of 2-[2-(3,5-dimethyl)pyridylmethylthio]-5-cyclopropylmethyloxybenzimidazole. To this was gradually added 1.38 g (0.008 mole) of m-chloroperbenzoic acid for a period of 15 minutes at 5° to 10° C. After the completion of the addition, the reaction mixture was stirred for additional 30 minutes at the same temperature and then washed with 100 ml of aqueous 10% sodium carbonate solution. The chloroform layer was separated, dried over anhydrous sodium sulfate, and then evaporated to dryness under reduced pressure. The residue obtained was subjected to silica gel column chromatography employing chloroform as the development solvent, and the fractions containing the desired compound were collected. The fractions were evaporated to dryness under reduced pressure. The residue obtained was recrystallized from a mixture of chloroform and ethyl ether to give 2.06 g (yield: 72.4%) of colorless crystals of 2-[2-(3,5-dimethyl)pyridylmethylsulfinyl]-5-cyclopropylmetyloxybenzimidazole.

Melting point: 132°–133° C.

IR absorption spectrum (KBr, cm$^{-1}$): 1010 (S=O)

Elementary analysis (%): Calcd for $C_{19}H_{21}N_3O_2S$: C, 64.20; H, 5.96; N, 11.82. Found: C, 64.16; H, 5.83; N, 11.79.

The compounds shown in Examples 2 to 5 were prepared in a similar manner as above, except that corresponding sulfide compounds [II] (0.008 mole) were used in place of 2-[2-(3,5-dimethyl)pyridylmethylthio]-5-cyclopropylmethyloxybenzimidazole (0.008 mole) and minor changes were made on the reaction temperature and the reaction time.

EXAMPLE 2

2-[2-(4-methyl)pyridylmethylsulfinyl]-5-cyclopropylbenzimidazole.

Colorless crystals; Yield, 1.79 g (65.5%)

Melting point: 93°–94° C. (recrystallized from ethyl ether)

IR absorption spectrum (KBr, cm$^{-1}$): 1030 (S=O)

Elementary analysis (%): Calcd. for $C_{18}H_{19}N_3O_2S$: C, 63.32; H, 5.61; N, 12.31. Found: C, 63.41; H, 5.57; N, 12.25.

EXAMPLE 3

2-[2-(3,5-dimethyl)pyridylmethylsulfinyl]-4-cyclopropylmethyloxybenzimidazole.

Colorless crystals; Yield, 2.44 g (85.8%)

Melting point: 139°–141° C. (recrystallized from ethyl ether)

IR absorption spectrum (KBr, cm$^{-1}$): 1040 (S=O )

Elementary analysis (%): Calcd. for $C_{19}H_{21}N_3O_2S$: C, 64.20; H, 5.96; N, 11.82. Found: C, 64.28; H, 5.81; N, 11.76.

EXAMPLE 4

2-[2-(3,4,5-trimethyl)pyridylmethylsulfinyl]-5-cyclopropylmethyloxybenzimidazole.

Light brown crystals; Yield, 2.12 g (71.7%)

Melting point: 181°–185° C. (recrystallized from a mixture of chloroform and ethyl ether)

IR absorption spectrum (KBr, cm$^{-1}$): 1010 (S=O)

Elementary analysis (%): Calcd. for $C_{20}H_{23}N_3O_2S$: C, 65.01; H, 6.27; N, 11.38. Found: C, 64.94; H, 6.19; N, 11.41.

EXAMPLE 5

2-[2-(3,4,5-trimethyl)pyridylmethylsulfinyl]-4-cyclopropylmethyloxybenzimidazole.

Colorless crystals; Yield: 2.18 g (73.7%)

Melting point: 166°–169° C. (recrystallized from a mixture of chloroform and ethyl ether)

IR absorption spectrum (KBr, cm$^{-1}$): 1040 (S=O)

Elementary analysis (%): Calcd. for $C_{20}H_{23}N_3O_2S$: C, 65.01; H, 6.27; N, 11.38. Found: C, 65.23; H, 6.35; N, 11.12.

EXAMPLE 6

In 80 ml of dichloromethane was dissolved 2.96 g (0.008 mole) of 2-[2-(4-methoxy-3,5-dimethyl)pyridylmethylthio]-4-cyclopropylmethyloxybenzimidazole. To this was added 40 ml of dichloromethane solution of 1.38 g (0.008 mole) of m-chloroperbenzoic acid for a period of 5 minutes at a constant temperature of −5° C. After the completion of the addition, the reaction mixture was stirred for additional 10 minutes at the same temperature and then washed with 50 ml of aqueous 1% sodium hydroxide solution. The dichloromethane layer was separated, dried over anhydrous sodium sulfate, condensed under reduced pressure, and then added with an appropriate amount of a mixture of petroleum ether and ethyl ether to precipitate crystals. The thus obtained crystals were recrystallized from a mixture of chloroform and ethyl ether to give 2.32 (yield: 75.3%) of colorless crystals of 2-[2-(4-methoxy-3,5-dimethyl)-pyridylmethylsulfinyl]-4-cyclopropylmethyloxybenzimidazole.

Melting point: 142°–146° C.
IR absorption spectrum (KBr, cm$^{-1}$): 1040 (S=O)
Elementary analysis (%): Calcd. for $C_{20}H_{23}N_3O_3S$: C, 62.31; H, 6.01; N, 10.90. Found: C, 62.28; H, 6.09; N, 10.99.

The compounds shown in Examples 7 to 9 were prepared in a similar manner as above, except that corresponding sulfide compounds [II] (0.008 mole) were used in place of 2-[2-(4-methoxy-3,5-dimethyl)pyridylmethylthio]-4-cyclopropylmethyloxybenzimidazole (0.008 mole) and minor changes were made on the reaction temperature and the reaction time.

EXAMPLE 7

2-[2-(4-methoxy-3,5-dimethyl)pyridylmethylsulfinyl]-5-cyclopropylmethyloxybenzimidazole.

Colorless crystals; Yield: 2.51 g (81.4%)
Melting point: 107°–108° C. (recrystallized from a mixture of chloroform and ethyl ether)
IR absorption spectrum (KBr, cm$^{-1}$): 1000 (S=O)
Elementary analysis (%): Calcd. for $C_{20}H_{23}N_3O_3S$: C, 62.31; H, 6.01; N, 10.90. Found: C, 62.19; H, 5.94; N, 10.84.

EXAMPLE 8

2-[2-(4-methoxy-5-methyl)pyridylmethylsulfinyl]-5-cyclopropylmethyloxybenzimidazole.

Colorless crystals; Yield: 1.73 g (58.2%)
Melting point: 139°–141° C. (recrystallized from a mixture of chloroform and ethyl ether)
IR absorption spectrum (KBr, cm$^{-1}$): 1030 and 1050 (S=O)
Elementary analysis (%): Calcd. for $C_{19}H_{21}N_3O_3S$: C, 61.43; H, 5.70; N, 11.31. Found: C, 61.32; H, 5.63; N, 11.40.

EXAMPLE 9

2-[2-(4-methoxy-5-methyl)pyridylmethylsulfinyl]-4-cyclopropylmethyloxybenzimidazole.

Colorless crystals; Yield: 2.35 g (79.1%)
Melting point: 150°–152° C. (recrystallized from a mixture of chloroform and ethyl ether)
IR absorption spectrum (KBr, cm$^{-1}$); 1040 and 1050 (S=O)
Elementary analysis (%): Calcd. for $C_{19}H_{21}N_3O_3S$: C, 61.43; H, 5.70; N, 11.31. Found: C, 61.51; H, 5.64; N, 11.42.

PREPARATION EXAMPLE 1:

(Tablets)

|  | % By Weight |
| --- | --- |
| (1) Compound prepared in Example 1 | 25 |
| (2) Lactose | 41 |
| (3) Corn starch powders | 15 |
| (4) Crystalline cellulose | 15 |
| (5) Hydroxypropyl cellulose | 3 |
| (6) Magnesium stearate | 1 |
|  | 100 |

The above ingredients (1) to (5) were mixed, granulated with the addition of water, and then dried. The thus obtained granules were regulated, mixed with the ingredient (6), and then formed with compression into tablets of 100 mg.

PREPARATION EXAMPLE 2

(Capsules)

|  | % By Weight |
| --- | --- |
| (1) Compound prepared in Example 8 | 25 |
| (2) Lactose | 50 |
| (3) Corn starch powders | 20 |
| (4) Hydroxypropyl cellulose | 3 |
| (5) Synthetic aluminium silicate | 1 |
| (6) Magnesium stearate | 1 |
|  | 100 |

Granules were prepared from the above ingredients according to conventional method. Capsules containing 100 mg of the granules were prepared therefrom.

What is claimed is:

1. A benzimidazole derivative represented by formula

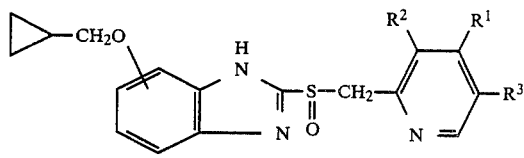

wherein $R^1$ is a hydrogen atom, a methyl group or a methoxy group, and $R^2$ and $R^3$ each is a hydrogen atom or a methyl group, at least one of said $R^1$, $R^2$ and $R^3$ groups being a member other than a hydrogen atom.

2. A compound as claimed in claim 1 wherein the cyclopropylmethyloxy group is substituted at the 4 or 5 position of the benzimidazole ring.

3. A compound as claimed in claim 2 wherein the substituted pyridyl group represented by the formula

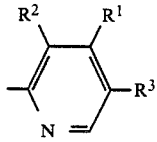

is selected from the group consisting of 2-(3,5-dimethyl)pyridyl, 2-(4-methyl)pyridyl, 2-(3,4,5-trimethyl)pyridyl, 2-(4-methoxy-3,5-dimethyl)pyridyl and 2-(4-methoxy-5-methyl)pyridyl.

4. 2-[2-(3,5-dimethyl)pyridylmethylsulfinyl]-5-cyclopropylmethyloxybenzimidazole.

5. 2-[2-(4-methyl)pyridylmethylsulfinyl]-5-cyclopropylmethyloxybenzimidazole.

6. 2-[2-(3,5-dimethyl)pyridylmethylsulfinyl]-4-cyclopropylmethyloxybenzimidazole.

7. 2-[2-(3,4,5-trimethyl)pyridylmethylsulfinyl]-5-cyclopropylmethyloxybenzimidazole.

8. 2-[2-(3,4,5-trimethyl)pyridylmethylsulfinyl]-4-cyclopropylmethyloxybenzimidazole.

9. 2-[2-(4-methoxy-3,5-dimethyl)pyridylmethylsulfinyl]-4-cyclopropylmethyloxybenzimidazole.

10. 2-[2-(4-methoxy-3,5-dimethyl)pyridylmethylsulfinyl]-5-cyclopropylmethyloxybenzimidazole.

11. 2-[2-(4-methoxy-5-methyl)pyridylmethylsulfinyl]-5-cyclopropylmethyloxybenzimidazole.

12. 2-[2-(4-methoxy-5methyl)pyridylmethylsulfinyl]-4-cyclopropylmethyloxybenzimidazole.

13. A sulfide compound represented by the formula

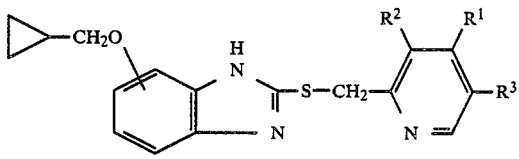

wherein $R^1$ is a hydrogen atom, a methyl group or a methoxy group, and $R^2$ and $R^3$ each is a hydrogen atom or a methyl group, at least one of said $R^1$, $R^2$ and $R^3$ groups being a member other than a hydrogen atom.

14. A compound as claimed in claim 13 wherein the cyclopropylmethoxy group is substituted at the 4 or 5 position of the benzimidazole ring.

15. A compound as claimed in claim 14 wherein the substituted pyridyl group represented by formula

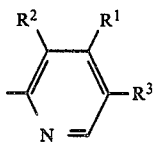

is selected from the group consisting of 2-(3,5-dimethyl)-pyridyl, 2-(4-methyl)pyridyl, 2-(3,4,5-trimethyl)-pyridyl, 2-(4-methoxy-3,5-dimethyl)pyridyl and 2-(4-methoxy-5-methyl)pyridyl.

16. 2-[2-(3,5-dimethyl)pyridylmethylthio]-5-cyclopropylmethyloxybenzimidazole.

17. 2-[2-(4-methyl)pyridylmethylthio]-5-cyclopropylmethyloxybenzimidazole.

18. 2-[2-(3,5-dimethyl)pyridylmethylthio]-4-cyclopropylmethyloxybenzimidazole.

19. 2-[2-(3,4,5-trimethyl)pyridylmethylthio]-5-cyclopropylmethyloxybenzimidazole.

20. 2-[2-(3,4,5-trimethyl)pyridylmethylthio]-4-cyclopropylmethyloxybenzimidazole.

21. 2-[2-(4-methoxy-3,5-dimethyl)pyridylmethylthio]-4-cyclopropylmethyloxybenzimidazole.

22. 2-[2-(4-methoxy-3,5-dimethyl)pyridylmethylthio]-5-cyclopropylmethyloxybenzimidazole.

23. 2-[2-(4-methoxy-5-methyl)pyridylmethylthio]-5-cyclopropylmethyloxybenzimidazole.

24. 2-[2-(4-methoxy-5-methyl)pyridylmethylthio]-4-cyclopropylmethyloxybenzimidazole.

25. A pharmaceutical composition usable for the treatment of ulcer comprising an effective dosage of from 0.5 to 2,000 mg of a benzimidazole derivative of claim 1, per day, and one or more physiological harmless pharmaceutical carriers.

26. A pharmaceutical composition claimed in claim 25 wherein the effective dosage in oral administration is an amount, of from 3 to 200 mg, per day.

27. A pharmaceutical composition claimed in claim 26 wherein the ulcer is gastric and/or duodenal ulcers.

28. A pharmaceutical composition claimed in any one of claims 25 to 27 wherein the benzimidazole derivative of claim 1 is 2-[2-(3,5-dimethyl)pyridylmethylsulfinyl]-5-cyclopropylmethyloxybenzimidazole.

29. A pharmaceutical composition claimed in any one of claims 25 to 27 wherein the benzimidazole derivative of claim 1 is 2-[2-(3,5-dimethyl)pyridylmethylsulfinyl]-4-cyclopropylmethyloxybenzimidazole.

30. A pharmaceutical composition claimed in any one of claims 25 to 27 wherein the benzimidazole derivative of claim 1 is 2-[2-(3,4,5-trimethyl)pyridylmethylsulfinyl]-5-cyclopropylmethyloxybenzimidazole.

31. A pharmaceutical composition claimed in any one of claims 25 to 27 wherein the benzimidazole derivative of claim 1 is 2-[2-(4-methoxy-5-methyl)pyridylmethylsulfinyl]-5-cyclopropylmethyloxybenzimidazole.

32. A method for treating ulcer of a person comprising administering an effective amount orally a pharmaceutical composition of claim 25.

33. A method as claimed in claim 32 wherein the ulcer is gastric and/or duodenal ulcers.

34. A method as claimed in claim 33 wherein the treatment is carried out 1 to 6 times a day.

* * * * *